(12) United States Patent
Arnold et al.

(10) Patent No.: US 9,629,662 B2
(45) Date of Patent: Apr. 25, 2017

(54) SPINAL ANCHORING SCREW

(71) Applicant: DePuy Synthes Products, Inc., Raynham, MA (US)

(72) Inventors: Benjamin Arnold, San Diego, CA (US); Seungkyu Daniel Kwak, Grafton, MA (US); John Riley Hawkins, Cumberland, RI (US); Erasmo A. Lopez, Seattle, WA (US); Missoum Moumene, Newton, MA (US); Charles M. Bartish, Jr., Providence, RI (US); William L. Dunbar, Jr., Bethlehem, CT (US); Amie Borgstrom, Stanford, CA (US); Anwar M. Upal, Fall River, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 681 days.

(21) Appl. No.: 13/798,243

(22) Filed: Mar. 13, 2013

(65) Prior Publication Data
US 2013/0197583 A1    Aug. 1, 2013

Related U.S. Application Data

(62) Division of application No. 11/646,961, filed on Dec. 28, 2006, now Pat. No. 8,409,256.

(51) Int. Cl.
*A61B 17/70* (2006.01)
*A61B 17/00* (2006.01)

(52) U.S. Cl.
CPC ...... *A61B 17/7035* (2013.01); *A61B 17/7004* (2013.01); *A61B 17/704* (2013.01);
(Continued)

(58) Field of Classification Search
CPC ................ A61B 17/70–17/7046
(Continued)

(56) References Cited

U.S. PATENT DOCUMENTS 4,257,409 A * 3/1981 Bacal ............... A61B 17/7052
411/437
4,269,178 A * 5/1981 Keene ........................ 606/276
(Continued)

FOREIGN PATENT DOCUMENTS

EP        0732081      9/1996
EP       1 579 816     9/2005
(Continued)

OTHER PUBLICATIONS

Supplementary European Search Report in corresponding European patent application (i.e. EP 07 86 3062), mailed Nov. 25, 2011 (11 pages).
(Continued)

*Primary Examiner* — Jan Christopher Merene
*Assistant Examiner* — Steven Cotroneo
(74) *Attorney, Agent, or Firm* — Maginot, Moore & Beck, LLP

(57) ABSTRACT

A spine stabilization system includes at least one bone anchor assembly, the bone anchor assembly including a bone engaging member and a receiver member, wherein the receiver member includes a connecting member cavity, and an elongated connecting member inserted into the connecting member cavity and connected to the receiver member, wherein the connecting member comprises locking features configured to secure the connecting member to the receiver member without the use of a fixation screw extending through a top portion of the receiver member.

10 Claims, 18 Drawing Sheets

(52) U.S. Cl.
CPC ...... *A61B 17/7005* (2013.01); *A61B 17/7013* (2013.01); *A61B 17/7028* (2013.01); *A61B 17/7032* (2013.01); *A61B 17/7037* (2013.01); *A61B 17/7038* (2013.01); *A61B 2017/00867* (2013.01)

(58) Field of Classification Search
USPC ........ 606/86 A, 246, 254–279; 403/329, 397
See application file for complete search history.

(56) References Cited

U.S. PATENT DOCUMENTS

| | | | |
|---|---|---|---|
| 4,274,401 A * | 6/1981 | Miskew | A61B 17/7004 606/256 |
| 4,409,968 A * | 10/1983 | Drummond | 606/86 A |
| 4,661,028 A | 4/1987 | Sanger | |
| 5,002,542 A | 3/1991 | Frigg | |
| 5,010,879 A * | 4/1991 | Moriya et al. | 606/276 |
| 5,042,982 A * | 8/1991 | Harms et al. | 606/256 |
| 5,176,678 A * | 1/1993 | Tsou | A61B 17/7032 606/267 |
| 5,176,679 A * | 1/1993 | Lin | 606/272 |
| 5,176,680 A | 1/1993 | Vignaud et al. | |
| 5,207,678 A | 5/1993 | Harms et al. | |
| 5,281,222 A * | 1/1994 | Allard | A61B 17/7032 606/264 |
| 5,282,863 A * | 2/1994 | Burton | 606/254 |
| 5,344,422 A | 9/1994 | Frigg | |
| 5,360,431 A | 11/1994 | Puno et al. | |
| 5,423,818 A * | 6/1995 | Van Hoeck et al. | 606/278 |
| 5,429,639 A | 7/1995 | Judet | |
| 5,466,238 A * | 11/1995 | Lin | 606/264 |
| 5,474,555 A | 12/1995 | Puno et al. | |
| 5,476,462 A * | 12/1995 | Allard et al. | 606/60 |
| 5,569,246 A | 10/1996 | Ojima et al. | |
| 5,575,792 A * | 11/1996 | Errico | A61B 17/7037 606/266 |
| 5,584,831 A | 12/1996 | McKay | |
| 5,658,286 A * | 8/1997 | Sava | 606/279 |
| 5,672,176 A | 9/1997 | Biedermann et al. | |
| 5,716,356 A | 2/1998 | Biedermann et al. | |
| 5,728,098 A | 3/1998 | Sherman et al. | |
| 5,776,135 A | 7/1998 | Errico et al. | |
| 5,879,350 A | 3/1999 | Sherman et al. | |
| 5,910,142 A | 6/1999 | Tatar | |
| 5,928,231 A * | 7/1999 | Klein | A61B 17/7049 606/218 |
| 5,938,663 A | 8/1999 | Petreto | |
| 5,954,725 A | 9/1999 | Sherman et al. | |
| 5,984,923 A | 11/1999 | Breard | |
| 6,053,917 A | 4/2000 | Sherman et al. | |
| 6,063,089 A | 5/2000 | Errico et al. | |
| 6,063,090 A | 5/2000 | Schlapfer | |
| 6,083,226 A | 7/2000 | Fiz | |
| 6,248,105 B1 | 6/2001 | Schlapfer et al. | |
| 6,471,705 B1 | 10/2002 | Biedermann et al. | |
| 6,485,491 B1 | 11/2002 | Farris et al. | |
| 6,520,963 B1 | 2/2003 | McKinley | |
| 6,641,586 B2 | 11/2003 | Varieur | |
| 6,695,843 B2 | 2/2004 | Biedermann et al. | |
| 6,723,100 B2 | 4/2004 | Biedermann et al. | |
| 6,755,829 B1 | 6/2004 | Bono et al. | |
| 6,802,844 B2 | 10/2004 | Ferree | |
| 6,827,719 B2 * | 12/2004 | Ralph et al. | 606/272 |
| 6,843,791 B2 | 1/2005 | Serhan | |
| 6,905,500 B2 | 6/2005 | Jeon et al. | |
| 6,932,822 B2 | 8/2005 | Oribe et al. | |
| 7,018,378 B2 | 3/2006 | Biedermann et al. | |
| 7,625,394 B2 | 12/2009 | Molz, IV et al. | |
| 7,686,833 B1 | 3/2010 | Muhanna et al. | |
| 7,867,256 B2 * | 1/2011 | Schlaepfer | 606/257 |
| 2002/0082602 A1 | 6/2002 | Biedermann et al. | |
| 2002/0111626 A1 * | 8/2002 | Ralph et al. | 606/61 |
| 2003/0100896 A1 | 5/2003 | Biedermann et al. | |
| 2003/0149431 A1 | 8/2003 | Varieur | |
| 2003/0158552 A1 | 8/2003 | Jeon et al. | |
| 2003/0220642 A1 * | 11/2003 | Freudiger | 606/61 |
| 2004/0186474 A1 | 9/2004 | Matthis et al. | |
| 2004/0225289 A1 | 11/2004 | Biedermann et al. | |
| 2004/0236327 A1 | 11/2004 | Paul et al. | |
| 2004/0236328 A1 | 11/2004 | Paul et al. | |
| 2004/0236329 A1 | 11/2004 | Panjabi | |
| 2004/0260284 A1 | 12/2004 | Parker | |
| 2005/0033295 A1 * | 2/2005 | Wisnewski | 606/61 |
| 2005/0143823 A1 | 6/2005 | Boyd et al. | |
| 2005/0154390 A1 | 7/2005 | Biedermann et al. | |
| 2005/0171543 A1 | 8/2005 | Timm et al. | |
| 2005/0177164 A1 | 8/2005 | Walters et al. | |
| 2005/0182400 A1 | 8/2005 | White | |
| 2005/0182401 A1 | 8/2005 | Timm et al. | |
| 2005/0182409 A1 | 8/2005 | Callahan et al. | |
| 2005/0203516 A1 | 9/2005 | Biedermann et al. | |
| 2005/0216003 A1 | 9/2005 | Biedermann et al. | |
| 2005/0277919 A1 | 12/2005 | Slivka et al. | |
| 2006/0142758 A1 | 6/2006 | Petit | |
| 2006/0149237 A1 | 7/2006 | Markworth et al. | |
| 2006/0217718 A1 | 9/2006 | Chervitz et al. | |
| 2006/0241600 A1 | 10/2006 | Ensign et al. | |
| 2007/0055244 A1 | 3/2007 | Jackson | |
| 2008/0161859 A1 | 7/2008 | Nilsson | |
| 2008/0177332 A1 | 7/2008 | Reiley et al. | |
| 2008/0183214 A1 | 7/2008 | Copp et al. | |
| 2008/0183215 A1 | 7/2008 | Altarac et al. | |

FOREIGN PATENT DOCUMENTS

| | | |
|---|---|---|
| JP | 2003061972 | 3/2003 |
| JP | 2004521718 | 7/2004 |

OTHER PUBLICATIONS

Australian Office Action corresponding to application No. AU 2007342474, dated May 25, 2012 (3 pages).
International Search Report corresponding to application No. PCT/US2007/025862, mailed May 14, 2008 (7 pages).
Japanese Office Action corresponding to application No. JP 2009-544032, mailed Jun. 5, 2012 (English and Japanese language documents) (6 pages).

* cited by examiner

SPINAL ANCHORING SCREW

This application is a divisional of prior application Ser. No. 11/646,961, filed Dec. 28, 2006, (now U.S. Pat. No. 8,409,256, issued on Apr. 2, 2013), which is herein incorporated by reference in its entirety.

FIELD

This application relates to the field of spinal stabilization devices. In particular, this application relates to a posterior stabilization unit configured for use with a segmental unit of the spine.

BACKGROUND

Spinal surgeries are commonly used in the medical profession to treat spinal conditions that result when functional segmental units of the spine are moved out of proper position or otherwise damaged. Examples of procedures used to treat spinal conditions include disc replacement, laminectomy, and spinal fusion.

Following certain spinal procedures, such as spinal fusion, it is typically desirable to stabilize the spine by preventing movement between the vertebrae while the spine heals. This act of stabilizing the spine by holding bones in place during healing has greatly improved the success rate of spinal fusions and other procedures.

With spinal stabilization procedures, a combination of metal screws and rods creates a solid "brace" that holds the vertebrae in place. These devices are intended to stop movement from occurring between the vertebrae. These metal devices give more stability to the fusion site and allow the patient to be out of bed much sooner.

During the spinal stabilization procedure, pedicle screws are placed through the pedicles on the posterior portion of two or more vertebrae of the spinal column. The screws grab into the bone of the vertebral bodies, giving them a good solid hold on the vertebrae. Once the screws are placed on the vertebrae, they are attached to metal rods that connect all the screws together. When everything is bolted together and tightened, the assembly creates a stiff metal frame that holds the vertebrae still so that healing can occur.

Posterior dynamic stabilization (PDS) generally refers to such a stabilization procedure where dynamic rods are positioned between the pedicle screws. These dynamic rods can generally bend, extend, compress, or otherwise deform in order to allow some limited movement between the pedicle screws. By allowing this limited movement between the pedicle screws and the associated vertebrae, less strain is placed on adjoining, non-stabilized functional segmental units during patient movements. In addition, the dynamic rod generally decreases the stresses on the screw shank, minimizing the possibility of screw backout or related screw failures. However, even with dynamic rods, stresses are experienced by the screw shank which could potentially result in screw backout or related failures under the appropriate circumstances. Accordingly, it would be desirable to provide a PDS system capable of further protecting the screw-bone interface and reducing the chances of screw backout. For example, it would be advantageous to provide a PDS system with a flexible stabilization element that offers different kinematics and loading requirements from those stabilization elements found in the prior art. Such a stabilization element would offer additional options to the surgeon when traditional PDS stabilization elements appear problematic.

SUMMARY

Various embodiments of a dynamic screw for a spine stabilization system are disclosed herein. In one embodiment, a dynamic screw for a spine stabilization system comprises at least one bone anchor assembly comprising a bone engaging member and a receiver member. The bone engaging member may comprise a bone screw including a screw head retained within the receiver member and a screw shank extending from the receiver member. The screw head may be pivotably retained within the receiver member. An elongated connecting member is pivotably connected to the bone engaging member. The elongated connecting member may be provided as a rod spanning between two or more bone anchor assemblies. The elongated connecting member is pivotably connected to the receiver member of the bone anchor assembly.

In one embodiment, the pivotable connection between the elongated connection member and the receiver member is provided by a ball-shaped pivot member on the rod which engages a bearing surface provided within a cavity of the receiver member. Accordingly, the pivot point for the rod may be provided within the cavity in the receiver member. In one such embodiment, the rod may define an axis wherein the axis pivots about a pivot point on the axis when the rod pivots relative to the receiver member. In other embodiments, the pivot point of the rod is offset from the axis defined by the rod.

The rod may be a fixed length or adjustable to accommodate different segmental units and patients of different sizes. In the adjustable embodiment, the rod comprises a shaft with a flexible central portion and at least one adjustable end. The adjustable end may be provided by various means. For example, the adjustable end may include a post configured to slide within the shaft of the rod. In one embodiment, the adjustable end is configured to threadedly engage the shaft. In another embodiment, the adjustable end is comprised of a shape memory alloy.

When assembled, the spine stabilization system generally comprises at least two bone anchors with a rod extending between the two bone anchors. As mentioned above, each bone anchor includes a bone screw and a receiver member configured to retain the bone screw. The rod extends between the two receiver members. In one embodiment where the rod is fixed relative to the receiver members, the rod is adapted to bend when the receiver members move relative to one another. In another embodiment, the rod is pivotably connected to both the receiver members, and the rod is adapted to extend or compress when the receiver members move relative to one another.

In an alternative embodiment, one or more bone anchors of the spine stabilization system include an insert in the form of a retention member that acts to lock a bearing for the bone screw within the receiver member. To this end, the receiver member includes a screw head cavity and a rod cavity with an insert positioned between the screw head cavity and the rod cavity. The screw head cavity is configured to receive a bearing that engages the head of the bone screw with the screw shank extending from the receiver member. In one embodiment, the bone screw bearing is a split bearing. The insert is positioned between the rod cavity and the bearing member and is configured to secure the split bearing within the receiver member. The insert may be provided to fit within a groove formed in an interior sidewall of the receiver member. In this embodiment, the insert comprises a retaining ring that secures the split bearing within the screw cavity. In another embodiment, the insert is comprised of a compressible material positioned between the bearing member and the rod cavity. When the rod is positioned in the rod cavity, the insert is compressed against the bearing member, thus locking the bearing member within the screw cavity.

In yet another embodiment, the bone anchor assembly is configured with a low profile, wherein the rod is locked within the receiver member without the use of a fixation screw. In this embodiment, the bone anchor assembly includes a head and a screw shank extending from the head. The screw shank is pivotable with respect to the head. Furthermore, a rod cavity is formed within the head. The end of the rod includes features that lock the rod within the rod cavity when the rod is inserted into the rod cavity, thus connecting the rod to the head. For example, in one embodiment, the end of the rod comprises a plurality of fingers that may be flared to lock the rod within the rod cavity. The rod may also include a plurality of teeth that grasp or mesh with the rod cavity to further secure the rod within the cavity.

The above described features and advantages, as well as others, will become more readily apparent to those of ordinary skill in the art by reference to the following detailed description and accompanying drawings.

DESCRIPTION

Figure 1:
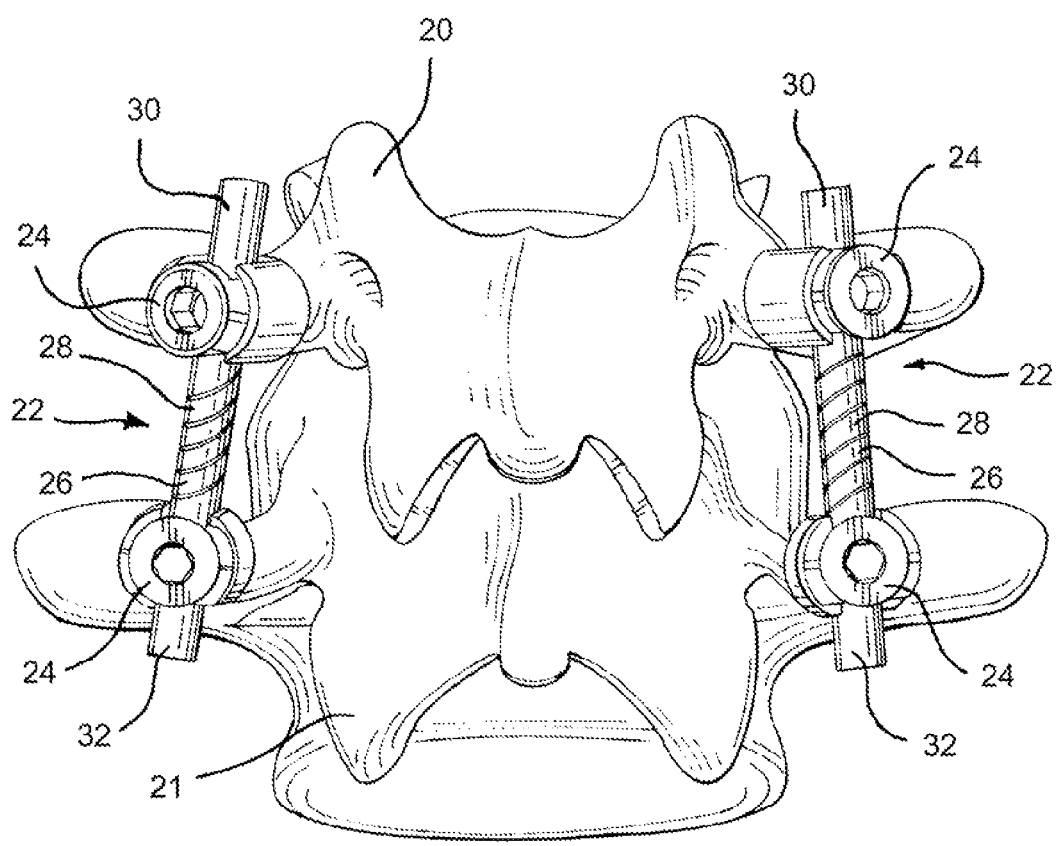
FIG. 1 shows a posterior view of a spine stabilization system with a plurality of dynamic screws and dynamic rods connected between two vertebrae.
Figure 2:
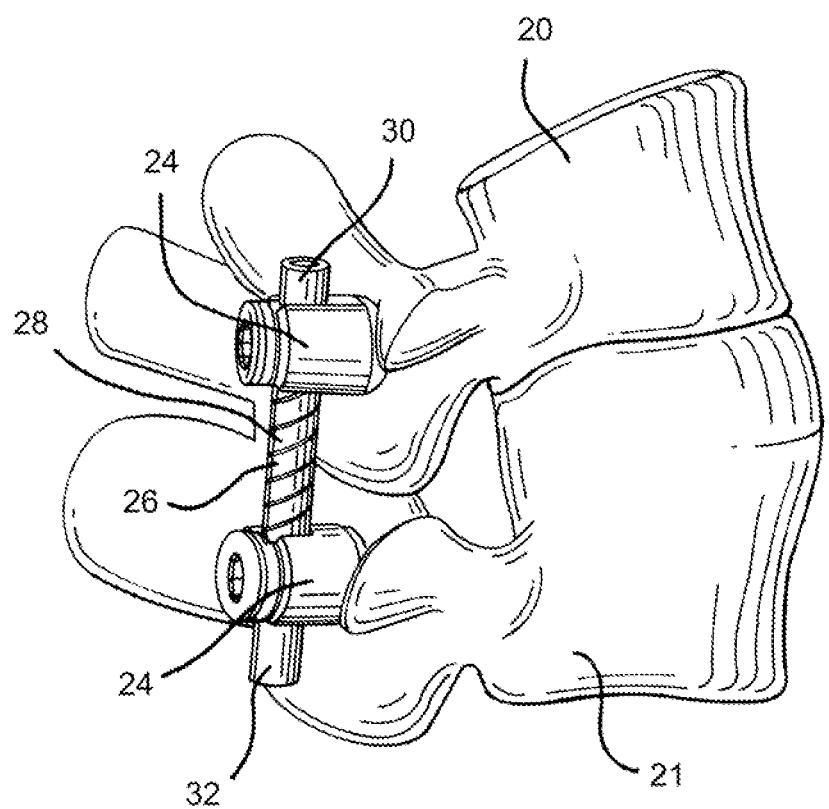
FIG. 2 shows a side view of the spine stabilization system of FIG. 1.

With reference to FIGS. 1 and 2, an exemplary posterior dynamic stabilization (PDS) system 22 is shown arranged between two vertebrae 20, 21 of a spine. The PDS system 22 comprises a plurality of bone anchors 24 with a plurality of elongated connecting members 26 extending between the bone anchors 24. The plurality of connecting members 26 may comprise rods, bars, or other elongated connecting members. Each bone anchor 24 is secured to the pedicle of one of the vertebrae 20 or 21. Each elongated connecting member 26 extends between a first bone anchor fixed to an upper vertebra 20 and a second bone anchor fixed to a lower vertebra 21.

The bone anchor 24 is comprised of titanium, stainless steel, or other appropriate biocompatible material. As explained in further detail herein, each bone anchor 24 comprises a bone engaging member 34, such as a bone screw (as shown in FIG. 3, for example). However, one of skill in the art will recognize that other bone engaging members 34 are possible, such as posts, pins, cemented surfaces, adhesive surfaces and other bone engaging members as are known in the art.

In addition to the bone engaging member 34, each bone anchor 24 also comprises a receiver member 40. The receiver member 40 is configured to receive a bone engaging member 34 and/or an elongated connecting member 26. If the bone engaging member 34 is a bone screw, the bone screw 34 includes a screw head 36 and a screw shank 38. The screw head 36 is retained within the receiver member 40 and the screw shank 38 extends from the receiver member 40. The screw shank 38 is configured to screw into the bone and secure the bone screw 34 to the pedicile or other portion of bone. The receiver member 40 may be rigidly or pivotably connected to the screw 34.

The receiver member 40 is also configured to receive an elongated connecting member, such as the rod 26. The rod 26 includes two rigid ends 30, 32 with an elastic/resilient central portion 28 disposed between the rod ends. The elastic central portion 28 allows for some limited flexibility in the rod, while still allowing the rod to spring back to its original shape. Therefore, when opposing forces are applied to the ends 30, 32 of the rod 26, the central portion flexes, allowing the rod to bend and/or elongate. When the opposing forces are removed, the rod returns to its original shape. With this configuration, the PDS system generally stabilizes two adjacent vertebrae, while still allowing for some limited movement between the vertebrae 20, 21. However, one of skill in the art will recognize that other types of rods are possible, including rigid rods or other flexible rods comprised of elastomeric material, metal, or superelastic material, or other types of PDS rods as are known in the art.

With reference now to FIGS. 3A-3D, one embodiment of a bone anchor assembly 24 is shown. In this embodiment, each bone anchor assembly 24 comprises a bone engaging member 34 retained within a receiver member 40. The bone engaging member is provided in the form of a bone screw 34 (which is also referred to herein as a "pedicle screw"). The bone screw 34 comprises a screw head 36 and a screw shank 38. The screw head 36 is generally spherical in shape with a flat top 39. A slot 37 is formed in the top of the screw head 36. The slot 37 is configured to receive the tip of a screwdriver that may be used to drive the screw 34 into the bone. The screw shank 38 extends from the screw head 36. The screw shank 38 is threaded to facilitate driving the screw into the bone.

In the embodiment of FIGS. 3A-3D, the receiver member 40 is a generally cup-shaped structure configured to hold both the screw 34 and the rod 26. The receiver member 40 comprises cylindrical sidewalls 42 formed between a superior end 44 and an inferior end 46. A bone screw cavity 48 is formed within the sidewalls 42 near the inferior end 46. A fixation screw cavity 50 is formed within the sidewalls 42 near the superior end 44. A rod cavity and passage 52 is formed in the receiver member between the fixation screw cavity 50 and the bone screw cavity 48.

The fixation screw cavity 50 is designed and dimensioned to receive a fixation screw 70 (also referred to herein as a setscrew). Accordingly, the cylindrical sidewalls 42 of the receiver member are threaded at the superior end 44. These threads are configured to engage the threads on the fixation screw 70. The fixation screw includes a slot 72 in the top that is adapted to receive the tip of a screwdriver, thus allowing the fixation screw 70 to be driven into the fixation screw cavity 50.

The rod passage 52 is provided directly below the fixation screw cavity 50. The rod passage is designed and dimensioned to receive one of the dynamic rods 26 of the PDS system 22. In particular, the rod passage 52 is designed to receive one of the rod ends 30. In the embodiment of FIG. 3, the rod is loaded into the rod passage from the top of the receiver member by laying the rod within U-shaped dips formed in the superior end 44 of the receiver member 40. After the rod 26 is positioned in the rod passage 52, a fixation screw is driven into the fixation screw cavity until it contacts the rod. When the fixation screw it tightened, it locks the rod in place within the receiver member 40. One of skill in the art will recognize that other appropriate locking features such as cam locks may be used to hold the rod in place.

The bone screw cavity 48 is designed and dimensioned to retain the screw head 36 of the bone screw 34, with the shank 38 of the bone screw extending from the receiver member 40. An opening 56 is formed in the inferior end 46 of the receiver member 40. In this disclosed embodiment, the diameter of the opening 56 is smaller than the diameter of the screw head 36, but it is large enough to allow the screw shank 38 to pass through the opening 56. Accordingly, the cylindrical wall 42 is slightly thicker at the inferior end 46 of the receiver member 40.

A bearing member 54 is positioned within the bone screw cavity 48 along with the screw head 36. The bearing member 54 includes an inner bearing surface that generally conforms to the spherical shape of the screw head 36. The screw head 36 is configured to rotate and pivot within the bearing member 54. The outer bearing surface is designed and dimensioned to engage the interior portion of the cylindrical sidewalls 42 of the receiver member.

Figure 3A:
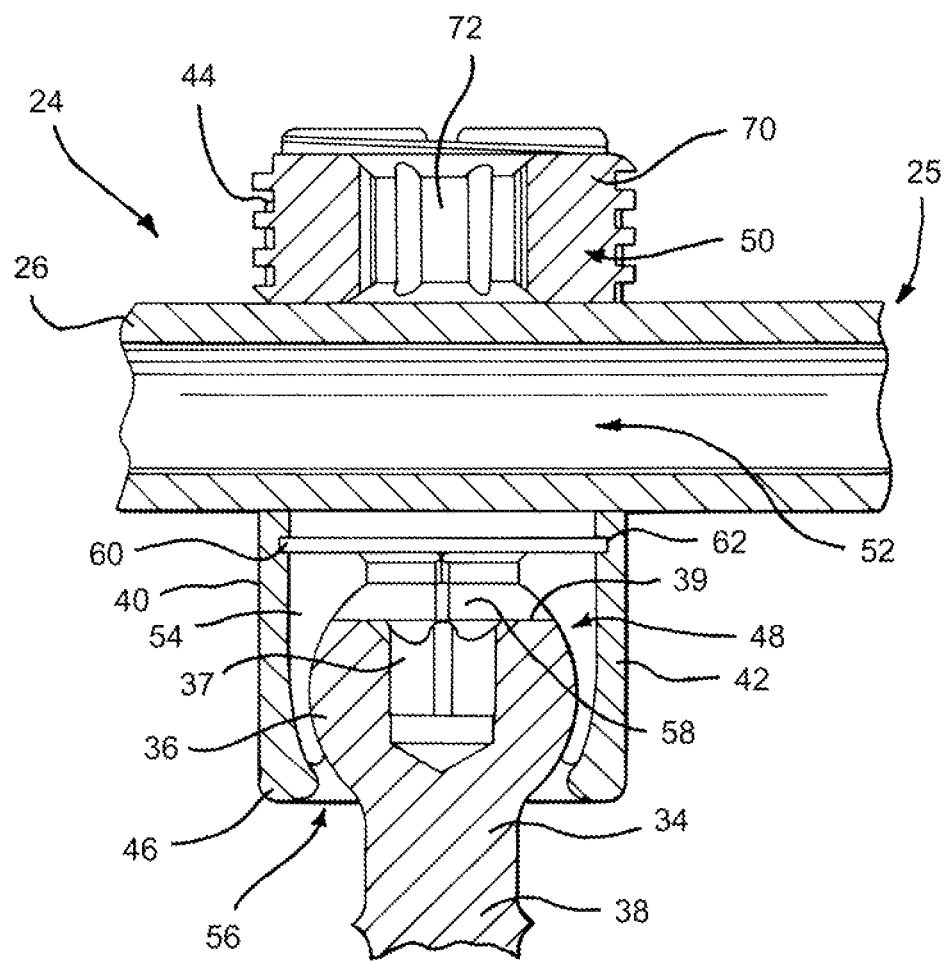
FIG. 3A shows a cross-sectional view of a bone anchor and rod which form part of the spine stabilization system of FIG. 1.
Figure 3B:
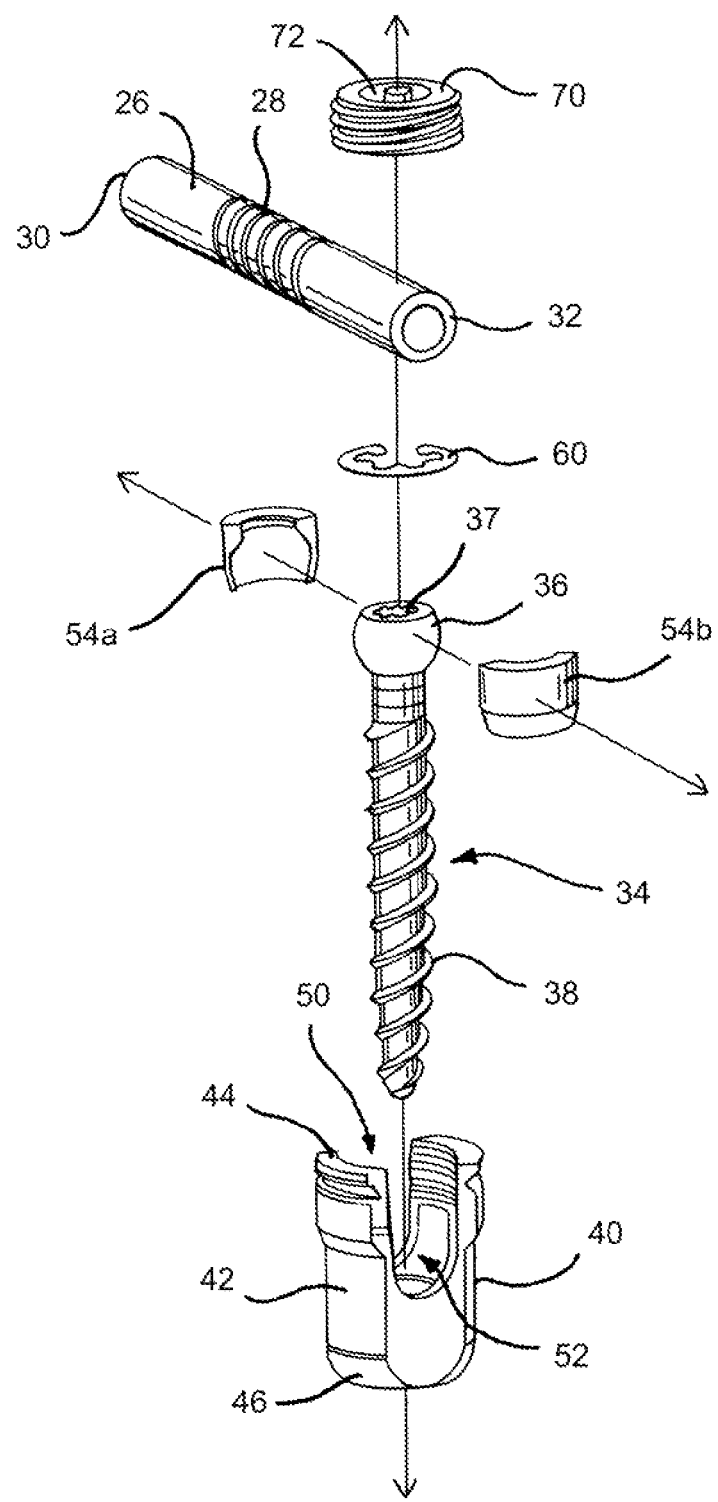
FIG. 3B shows an exploded perspective view of the bone anchor and rod of FIG. 3A.

In one embodiment, the bearing member 54 is a split bearing that includes a left side member 54a and a right side member 54b. The split bearing, 54a, 54b provides for easier assembly by allowing the bearing surface to be assembled around the spherical screw head 36. In addition, the split bearing members 54a, 54b facilitate the use of different bearing materials. Appropriate bearing materials will be recognized by those of skill in the art. In the embodiment of FIGS. 3A and 3B, the bearing members 54a, 54b are comprised of ceramic. Examples of other types of appropriate bearing materials include cobalt chrome, UHMWPE, and other biocompatible materials.

Figure 3C:
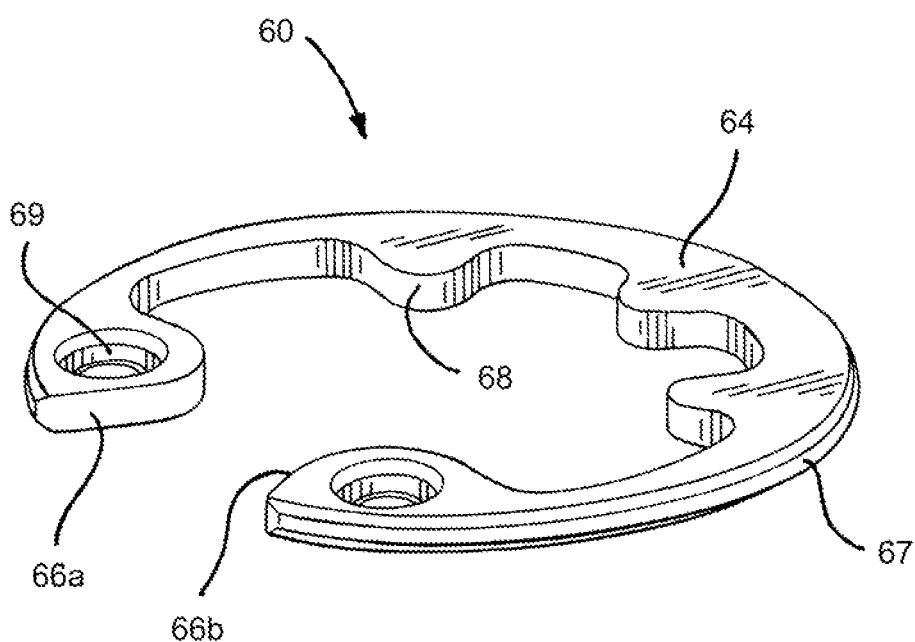
FIG. 3C shows a perspective view of a retainer insert of FIG. 3B.
Figure 3D:
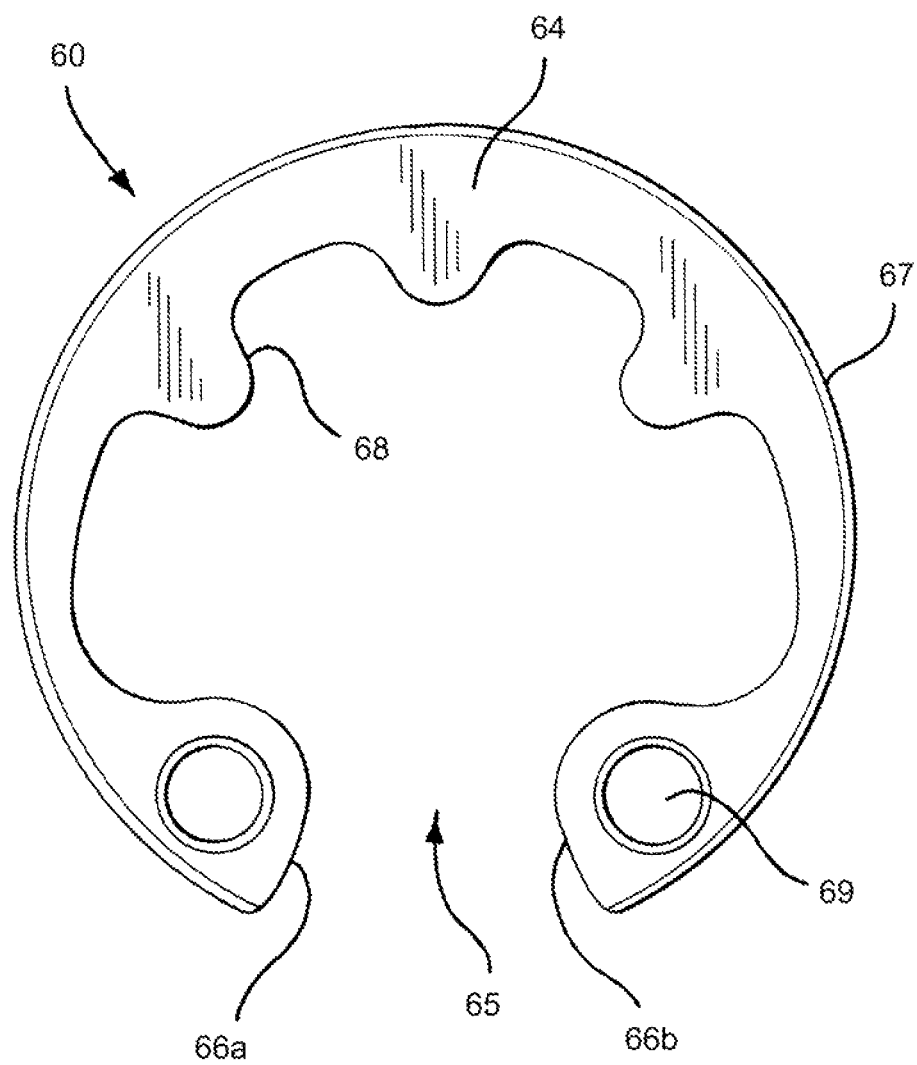
FIG. 3D shows a top view of the retainer insert of FIG. 3C.

An insert 60 is provided in the receiver member. The insert 60 acts as a retention member to secure the bearing member 54 in place within the bone screw cavity 48 of the receiver member 40. In the embodiment of FIGS. 3A-3D, the insert 60 is C-shaped plate that serves as a retaining ring. As best seen in FIGS. 3C and 3D, the insert 60 includes a semi-circular wall 64 with a void 65 formed in the wall. Two opposing ends 66a and 66b define the sides of the void 65. The exterior perimeter 67 of the insert 60 is generally circular in shape, while the interior perimeter 68 is contoured to provide strength to the insert. In addition, the insert may include other structural features such as holes 69. The insert 60 is generally comprised of a resilient biocompatible material, such as cobalt chrome or UHMWPE. The resilient features of the insert 60 allow the ends 66a, 66b to be forced together, reducing the size of the void 65, and then spring back to their original position.

As shown in FIG. 3A, the insert 60 is provided within a groove 62 formed in the cylindrical sidewalls 42 of the receiver member 40. With reference to the exploded view of the anchor assembly 24 shown FIG. 3B, it can be seen that the insert 60 is loaded into the retainer member 40 through a hole 50 in the top of the retainer member. First, the split bearing members 54a, 54b are positioned about the head of the screw 38 and the screw is inserted into the receiver member 40. Upon insertion, the split bearing members 54a, 54b and screw head 36 are seated in the screw head cavity and the shank 38 extends through the hole in the bottom of the receiver member 40. Next, the insert 60 is compressed and inserted into the receiver member 40. When properly positioned, the resilient insert snaps into the groove 62 in the receiver member, thus locking the split bearing members 54a, 54b in place within the retainer member. With the insert 60 locked in the groove 62, the bearing member 54 is secured in place within the receiver member such that various stresses on the bone screw will not dislodge the bearing member within the anchor assembly 24. After insertion of the insert 60, the rod 26 is placed in the rod passage 53 of the receiver member and the fixation screw 70 is threaded in the fixation screw cavity 50 until it compresses against the rod, thus fixing the rod to the receiver member 40.

Figure 4:
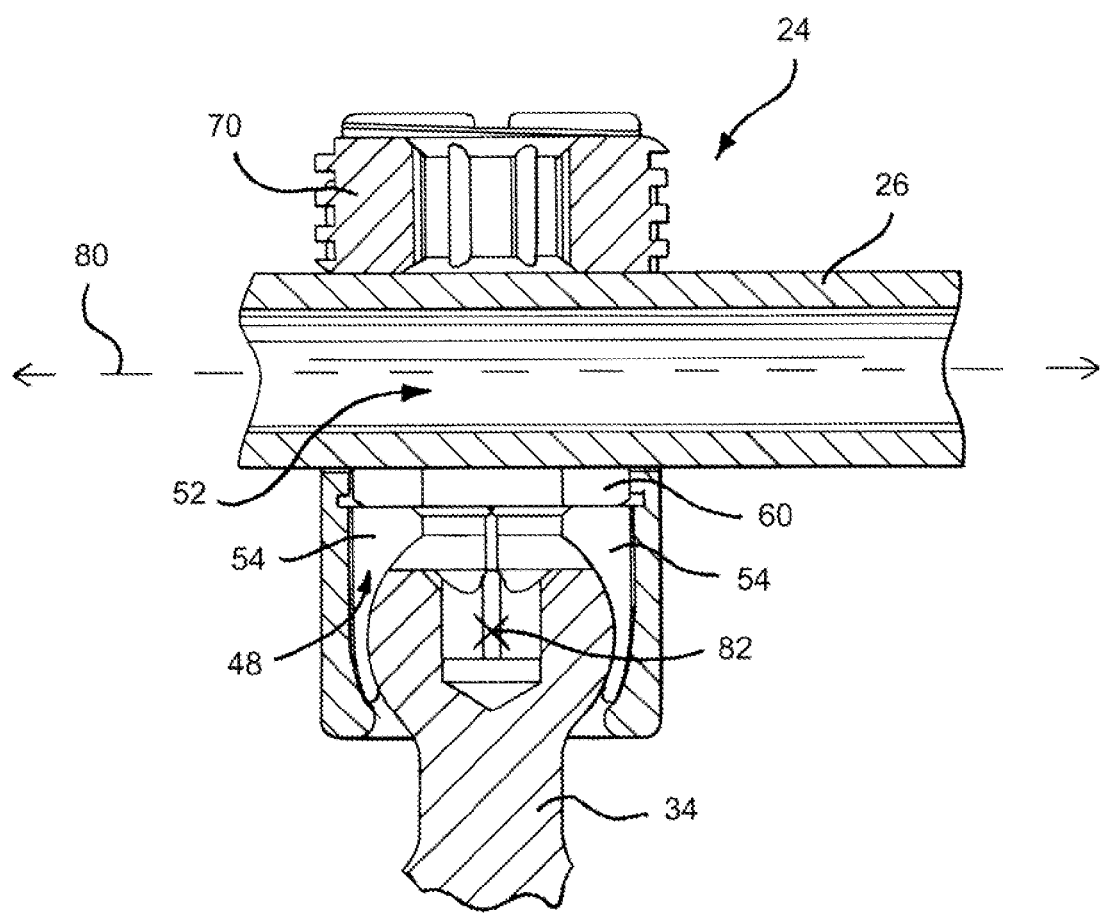
FIG. 4 shows a cross-sectional view of an alternative embodiment of the bone anchor and rod of FIG. 3.

FIG. 4 shows an alternative embodiment of a bone anchor assembly including an insert for securing the bearing 54 within the receiver member 40. In this embodiment, the insert 60 comprises a polyethylene disc positioned between the rod 26 and the bearing 54. Before the fixation screw is tightened, the top surface of the polyethylene disc 60 is positioned within the rod cavity 52. Thus, when the fixation screw 70 is tightened against the rod 26, the polyethylene insert 60 is slightly compressed by the rod. The force of this compression is then transferred to the bearing member 54, which is tightly compressed within the bone screw cavity 48, thus securing the bearing in place. Although FIGS. 3 and 4 show only two methods for holding the bearing 54 in place within the receiver member 40, one of skill in the art will recognize that variations of the disclosed embodiments may be easily incorporated. For example, in one embodiment, a combination retaining ring and compression disc may be used.

Rod Fixed to Receiver Member Providing With Pivot Point Offset from Rod Axis

From FIGS. 3 and 4, it can be seen that an offset exists between the center axis of the rod and the pivot point of the rod 26 within the anchor assembly 24. In particular, as shown in FIG. 4, the center axis 80 of the rod (shown by dotted line 80) is removed from the pivot point (shown by "X" 82) of the rod within the anchor assembly 24. This offset provides one embodiment that may be used to help control the necessary kinematics and loading requirements of the rod. In these embodiments, the rod 26 is fixed to the anchor assembly, and is not allowed to pivot relative to the receiver member 40 which holds the bone screw 34.

Figure 5:
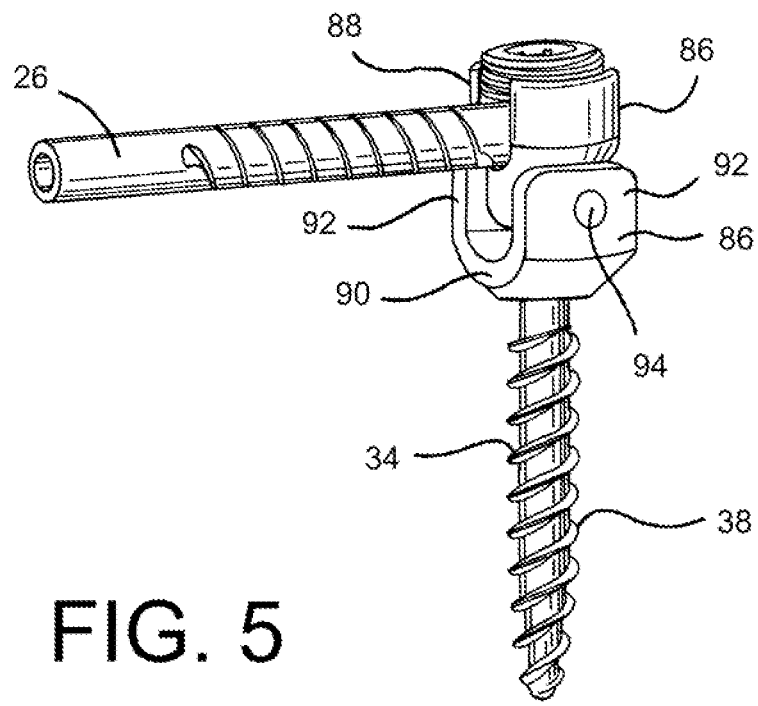
FIG. 5 shows a perspective view of an alternative embodiment of the bone anchor and rod of FIG. 3 wherein the pivot point of the rod is offset from the central axis of the rod.
Figure 6:
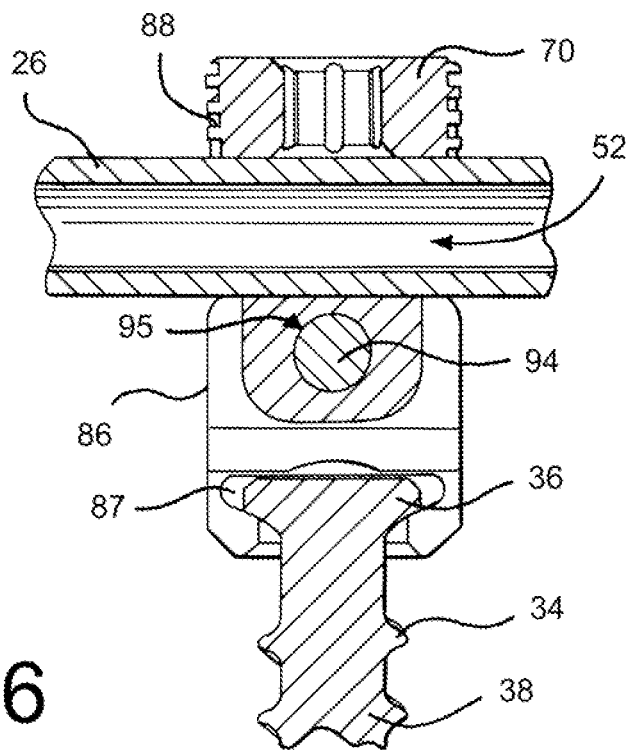
FIG. 6 shows a cross-sectional view of the bone anchor and rod of FIG. 5.

An alternative embodiment of a bone anchor 24 where the center axis of the rod is offset from the pivot point of the rod within the anchor assembly is shown in FIGS. 5 and 6. In this embodiment, the anchor assembly includes a bone screw 34, a U-shaped screw holder 86, and a rod holder 88. The bone screw includes a threaded shank 38, but instead of a spherical head, the head 36 of the bone screw is flat and generally circular or disc-shaped. This flat screw head is designed and dimensioned to fit within a circular cavity formed in the base 90 of the U-shaped screw holder 86. The circular cavity 87 allows the head 36 to rotate within the cavity 87 about the axis of the screw. A pivot pin 94 extends through the upright portions 92 of the U-shaped screw holder 86.

The rod holder 88 is pivotably mounted on the pivot pin 94. The rod holder 88 is similar to the receiver member 40 described in FIGS. 3 and 4. However, in place of a screw cavity, the rod holder 88 of FIGS. 5 and 6 includes a pin channel 95 configured to receive the pivot pin 94. The rod holder 88 is allowed to rotate about the pivot pin 94, thus allowing the rod holder 88 to pivot relative to the U-shaped screw holder 86. A rod passage 52 is formed in the rod holder 88 above the pin channel 95. A fixation screw 70 threadedly engages the interior threaded walls on the top of the rod holder 88. When the fixation screw 70 is tightened against the rod, the rod is pinned in place within the rod holder 88.

In the embodiment of FIGS. 5 and 6, the rod is allowed only two degrees of freedom. First, the rod 26 is allowed to pivot by radial rotation around an axis defined by the screw shank 38 by virtue of the rotatable engagement between the screw head 36 and the circular cavity 87 of the U-shaped screw holder 86. Second, the rod 26 is allowed to pivot about the pin 94 which is perpendicular to the screw shank. To facilitate rotation of the screw head 36 and the pin 94 within the U-shaped screw holder, the U-shaped screw holder may be comprised of ultra high molecular weight polyethylene (UHMWPE), cobalt chrome, titanium, stainless steel or other appropriate biocompatible bearing material as will be recognized by those of skill in the art.

Figure 7:
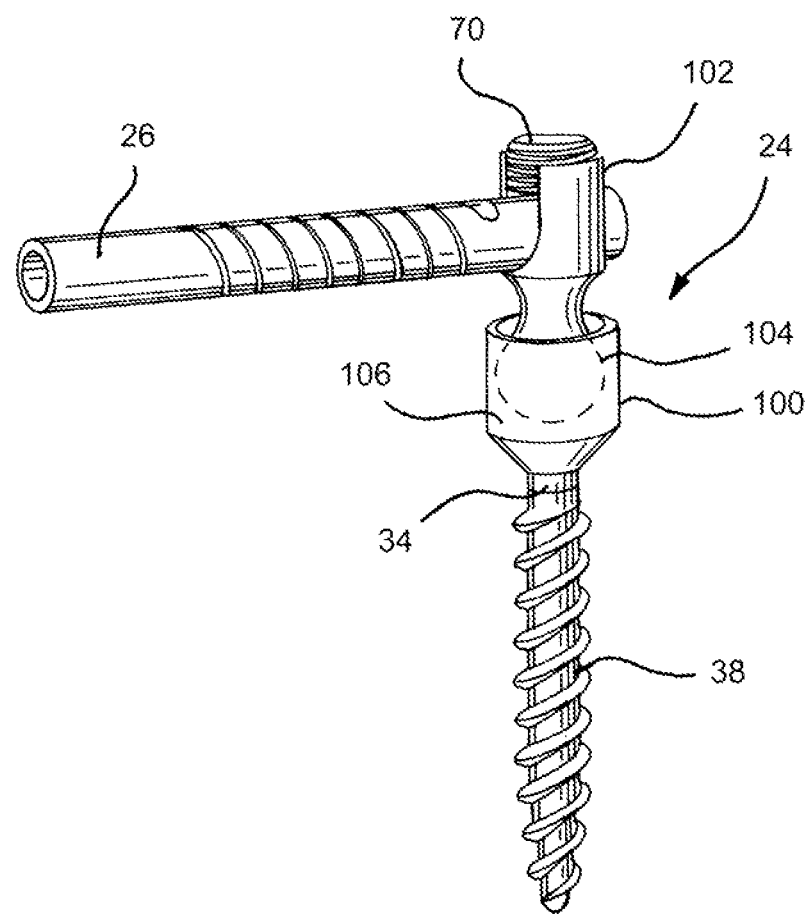
FIG. 7 shows an alternative embodiment of the bone anchor and rod of FIG. 5.

Another alternative embodiment of a bone anchor 24 where the center axis of the rod is offset from the pivot point of the rod is shown in FIG. 7. The bone anchor 24 of FIG. 7 includes a receiver member in the form of a screw holding member 100 that is fixed to the shank 38 of the bone screw 34. The rod 26 is secured to a rod holding member 102 which includes a cavity that receives the rod 26. The rod holding member 102 includes a fixation screw 70 that clamps onto the rod in order to fix to the rod holding member 102 to the rod 26. The rod holding member further includes a ball-shaped pivot member (shown by dotted lines 104 within the screw holding member 100). In this embodiment, the screw holding member 100 includes a cavity with a spherical bearing 106 and bearing surface that is also fixed relative to the screw shank 38. The spherical bearing surface is configured to receive the pivot member 104 which is fixed to the rod 26. Because the surface of the pivot member 104 is congruent with the bearing surface, the pivot member 104 is allowed to pivot within the screw holding member 100. Accordingly, the rod 26 is configured to pivot relative to the shank 38. The pivot point for the rod 26 is defined at the center of the pivot member 104 which is located within the center of the cavity in the screw holding member 100.

Rod Pivotably Connected to Receiver Member With Pivot Point on Rod Axis

Figure 8:
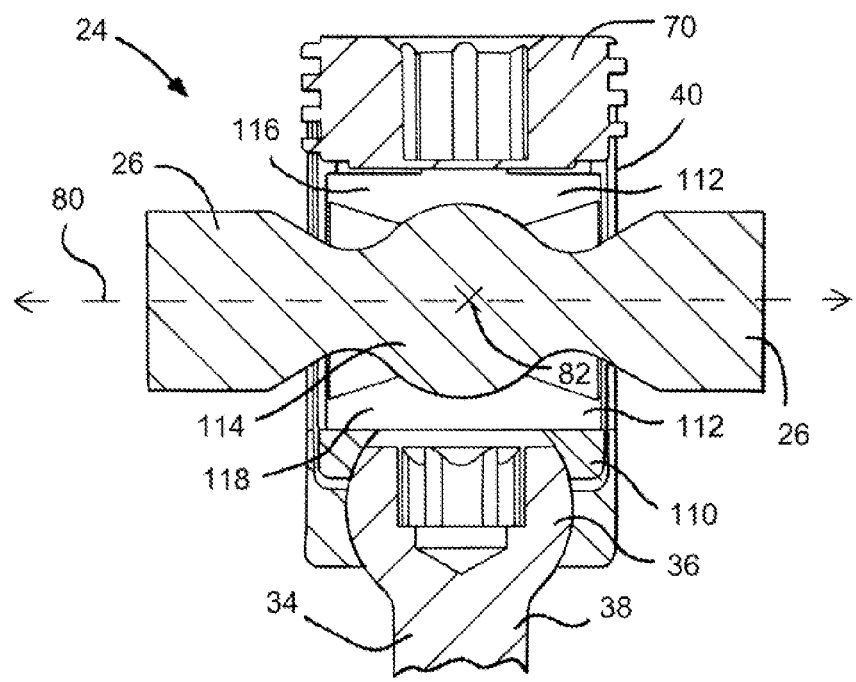
FIG. 8 shows a cross-sectional view of an alternative embodiment of the bone anchor and rod of FIG. 3 wherein the pivot point of the rod is provided on the central axis of the rod.
Figure 9:
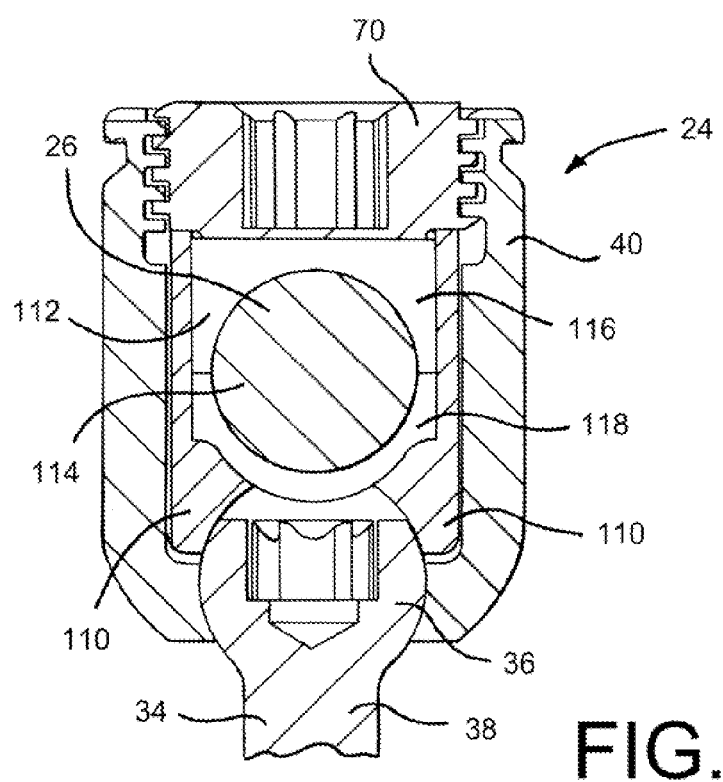
FIG. 9 shows another cross-sectional view of the bone anchor and rod of FIG. 8 rotated 90°.

With reference now to FIGS. 8-9, an alternative embodiment of a bone anchor 24 for a PDS system is shown where the rod 26 is pivotably connected to the receiver member 40 of the bone anchor. The bone anchor 24 includes a bone screw 34 having a screw head 36 retained within the receiver member 40 with the screw shank 38 extending from the receiver member 40.

Two different bearings are retained within the receiver member 40. In particular, a first bearing 110 provides a bearing surface for the screw head. The first bearing acts to stabilize the screw head 36 within the receiver member 40 while providing a surface upon which the screw head may pivot relative to the receiver member 40. In one embodiment, the first bearing may be comprised of a metallic insert that acts to lock the bone screw 34 in place when a fixation screw is tightened, as discussed in further detail below.

In addition to the first bearing 110, a second bearing 112 is also provided within the receiver member 40 shown in FIGS. 8 and 9. The second bearing 112 provides spherical bearing surface for the rod 26, allowing the rod 26 to pivot relative to the receiver member 40. Accordingly, the rod 26 includes a pivot member 114 in the form of a spherical ball fixed on at least one end of the rod 26. The spherical ball 114 engages the spherical bearing surface of the second bearing 112, thus pivotably retaining the rod 26 within the receiver member 40 and facilitating smooth movement of the rod relative to the receiver member. In this embodiment, the pivot member 114 is fixed to the rod 26, being integrally formed upon the rod.

In the embodiment disclosed in FIGS. 8 and 9, the second bearing 112 is a split bearing that includes a superior bearing member 116 provided above the spherical ball 114 and an inferior bearing member 118 provided below the spherical ball 114. In another alternative embodiment, the bearing is split into left and right halves such as the bearing shown in FIG. 3B. The split bearing 112 is comprised of UHMWPE, ceramic, cobalt chrome, or any other biocompatible material. In one alternative embodiment, the first bearing 110 and the inferior bearing member 118 of the second bearing 112 may be provided as a single integral component.

The components of the anchor assembly 24 may all be loaded into the receiver member 40 through a top hole. First, the bone screw 34 is inserted into the receiver member 40 with the screw head 36 seated in the screw head cavity and the shank 38 extending through the hole in the bottom of the receiver member 40. Second, the first bearing 110 is placed over the screw head. Next, the inferior bearing member 118 of the second bearing 112 is placed on top of the first bearing 110. The rod 26 is then placed in the receiver member with the spherical ball 114 engaging the bearing surface of the inferior bearing member 118, and the cylindrical portion of the rod passing through the rod passage formed in the sidewalls of the receiver member. The superior bearing member 116 is then placed over the spherical ball 114. This provides a superior bearing surface for the spherical ball. Finally, the fixation screw 70 is threaded into the top of the receiver member until it compresses against the second bearing member. Alternatively, the bearing components, screw, and rod may be pre-assembled and inserted into the receiver member as a unit.

In the embodiment of FIGS. 8 and 9, the anchor 24 acts as polyaxial screw that can be locked down by the metal insert 110 that is tightened by the fixation screw 70 when the screw head 36 is in the desired position. The fixation screw 70 functions to lock the bone screw 34 and to slightly compress the second bearing 112, thus keeping the second bearing in place within the receiver member 40.

In the embodiment of FIGS. 8 and 9, it can also be seen that the rod 26 is configured to pivot relative to the receiver member 40. Accordingly, as shown in FIG. 8, the pivot point 82 which the rod 26 pivots about is located on an axis defined by the rod and extending along the rod, such as a central axis 80 or an axis extending axially through the rod or along the surface of the elongated rod 26. In the case of FIG. 8, the axis is the central axis 80 of the rod. Because of this, the rod is constrained to motion in the axial direction. In other words, in this embodiment, the dynamic central portion of the rod is elongated or compressed, but is not bent when the receiver member 40 moves. Thus, for a given PDS assembly of two bone anchors and a rod, when the vertebrae move the bone screws 34, the receiver members 40 also move along with the bone screws. Because the rod 26 is allowed to pivot relative to the receiver members 40 about pivot point 82, movement of the receiver members 40 imparts axial forces on the rod 26 that cause the rod to either compress or elongate. Advantageously, this arrangement offers different kinematics and loading requirements from those stabilization elements where the pivot point is offset from an axis defined by the rod. These differing kinematics and loading requirements may be advantageous with certain materials and designs or with certain patients.

One alternative embodiment to that of FIGS. 8 and 9 involves the use of a setscrew nested in the fixation screw, allowing the polyaxial screw to be locked separate from the compression of the bearing surface. Furthermore, although there is a specific shape and locking of the bearing surface shown in FIG. 8, this could be altered based on materials used and the constraints of the rod. Of course one of skill in the art will recognize that numerous other adaptations of the embodiment of FIGS. 8 and 9 are possible where the pivot point of the rod is located along the central or other axis of the rod.

Figure 10:
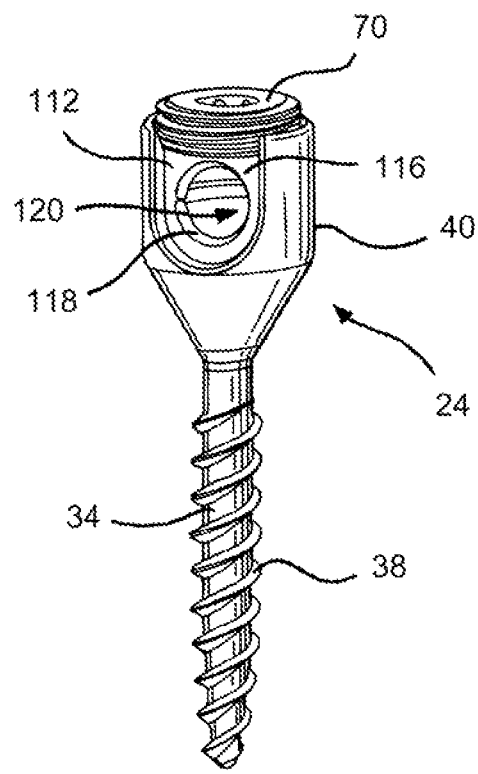
FIG. 10 shows a perspective view of an alternative embodiment of the bone anchor of FIG. 8.

Another example of an alternative embodiment for the bone anchor of FIGS. 8 and 9 is shown in FIG. 10. FIG. 10 shows an embodiment of a bone anchor 24 which acts as a fixed screw instead of a polyaxial screw. In particular, in FIG. 10, the screw shank 38 is fixed to the receiver member 40. In this embodiment, the screw shank 38 may be integrally formed with the receiver member 40 such that the receiver member 40 serves as the bone screw head. Alternatively, the screw shank 38 may be otherwise fixed to the receiver member 40 using some locking mechanism or other connection means. In the embodiment of FIG. 10, the inferior portion 118 of the bearing member 112 is first placed in the cavity 120 formed in the receiver member 40. The ball shaped portion of the rod 26 is then loaded onto the inferior bearing surface and the superior bearing member 116 is placed on top of the rod within the cavity. Finally, the fixation screw 70 is used to secure the bearing 112 within the cavity 120 of the receiver member 40.

Figure 11:
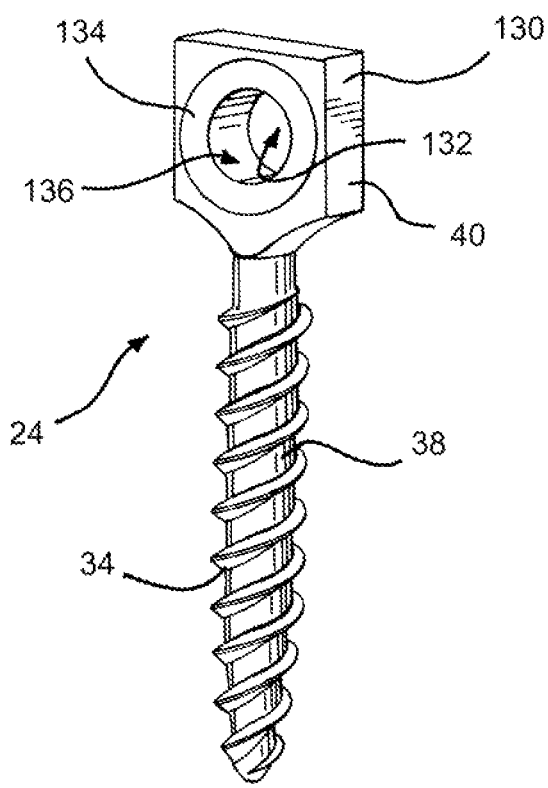
FIG. 11 shows a perspective view of another alternative embodiment of the bone anchor of FIG. 8.

FIG. 11 shows another embodiment, similar to FIG. 10, where the screw shank is fixed to the receiver member 40, and the screw head is formed as the receiver member 40. In FIG. 11, the receiver member 40 is formed as a block 130 with a central cavity 132. A bearing member 134 with a toroidal bearing surface 136 is positioned within the cavity 132 of the receiver member 40. Because the receiver member 40 is fixed relative to the screw shank 38, the bearing 134 is also fixed relative to the screw shank 38. The toroidal bearing surface is configured to receive a spherical portion on the end of a rod, similar to the rod end in FIGS. 8 and 9 that includes a spherical ball 114. Engagement of the spherical ball 114 and the toroidal bearing surface 136 allows the rod 26 to pivot relative to the shank 38 of the bone screw 38. In this embodiment, the bearing 134 is shown as being UHMWPE and as being held in place by a press fit. However, one of skill in the art will recognize that numerous other viable bearing materials and locking mechanisms may be used. Similar to the embodiments of FIGS. 8-10, the bone anchor disclosed in FIG. 11 provides an arrangement where the pivot point of the rod is located along the central axis of the rod.

Figure 12:
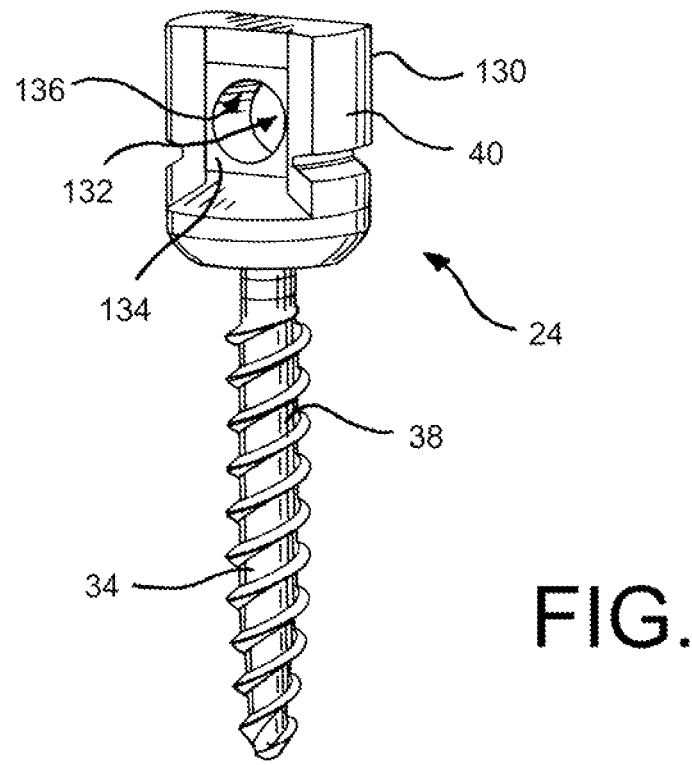
FIG. 12 shows a perspective view of another alternative embodiment of the bone anchor of FIG. 8.
Figure 13:
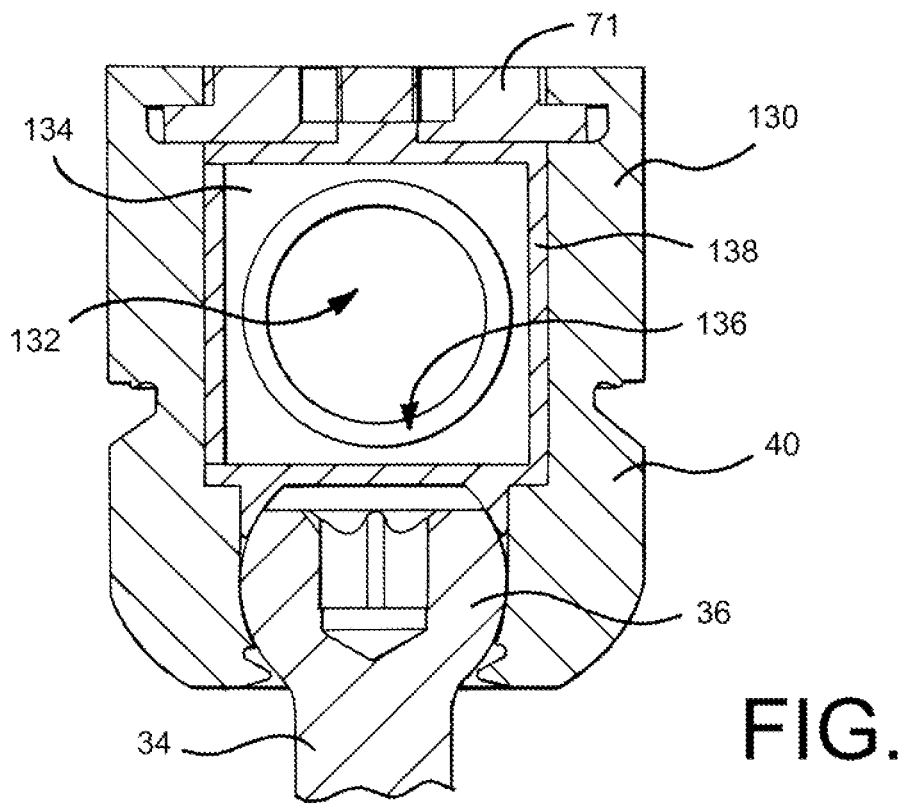
FIG. 13 shows a cross-sectional view of the bone anchor of FIG. 12.

FIGS. 12 and 13 show another alternative embodiment similar to FIG. 11. However, in the embodiment of FIGS. 12 and 13, the bearing 134 is not fixed relative to the screw shank 38. Instead, the bone anchor 24 acts as a polyaxial screw, and the bone screw head 36 and shank 38 are connected to the block 130/receiver member 40 in a pivotable relationship. Like the bone screw 34, the bearing 134 is loaded in the top of the receiver member 40, and a set screw or other locking member 71 holds the bearing 134 in place within the receiver member 40. Although the bone anchor acts as a polyaxial screw, the bone screw 34 can be locked in place relative to the block 130 when the locking member 71 is tightened within the block. Accordingly, a metal insert 138 may be provided around the bearing 134. When the locking member 71 is tightened, the metal insert 138 is locked into the screw head 36, fixing the bone screw relative to the block 130. One of skill in the art will recognize that various alternative versions of the embodiments of FIGS. 11-13 are possible. For example, it will be recognized that a dual setscrew could be used and that although the bearing surface is shown as a solid piece, it could be split to allow for easier assembly and to facilitate the use of other materials.

Figure 14:
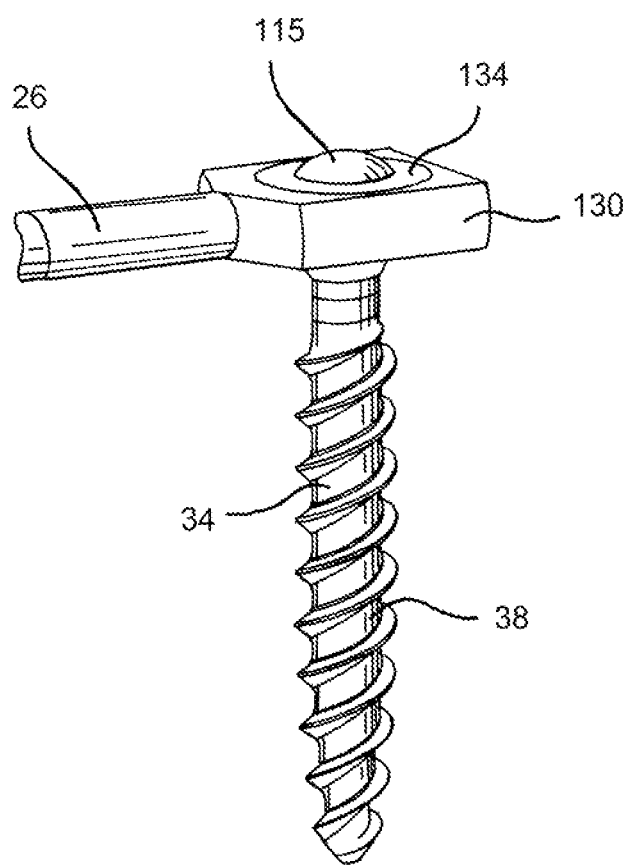
FIG. 14 shows a perspective view of yet another alternative embodiment of the bone anchor and rod of FIG. 8.

Yet another embodiment of a bone anchor 24 where the pivot point of the rod is located along the central axis of the rod is shown in FIG. 14. The embodiment of FIG. 14 is very similar to that of FIG. 11, but in FIG. 14 the block 130 and bearing 134 is provided on the rod 26 rather than the screw shank 38. Likewise, a spherical ball 115 is provided on the screw shank 138 rather than on the rod 26. The spherical ball 115 engages the bearing 134, allowing the rod 26 to pivot relative to the bone screw 34. In this embodiment, the bearing 134 is shown as being UHMWPE and as being held in place by a press fit. However, one of skill in the art will recognize that numerous other viable bearing materials and locking mechanisms may be used.

FIGS. 15A-15F show six possible designs for an adjustable length rod that could be used with the designs of FIGS. 8-13 where the pivot point of the rod is provided along the center axis of the rod. As mentioned above, adjustable length rods are advantageous when providing a PDS system so that different sized systems may be constructed for segmental units of different sizes and patients of different sizes. Accordingly, the rods of FIGS. 15A-15F may be used to provide an adjustable PDS system comprising: a plurality of bone anchors; and at least one connecting member connected to and extending between the plurality of bone anchors, wherein the at least one connecting member is adjustable in length. In one embodiment, the at least one connecting member is fixedly connected to the plurality of bone anchors. In another embodiment, the at least one connecting member is pivotably connected to the plurality of bone anchors. In other embodiments, the adjustable connecting member is provided as a telescoping shaft with two or more portions that slide relative to one another and may be locked to one another. In another embodiment, the adjustable connecting member comprises a shaft with a threaded ball on the end that can be turned to effectively lengthen or shorten the connecting member. These and other embodiments are shown in FIGS. 15A-15F. The embodiments of FIGS. 15A-15F show rods with helical dynamic portions provided in the center of the rod. However, it is intended that the embodiments disclosed herein could be used with any dynamic element, and not just helical dynamic portions.

Figure 15A:
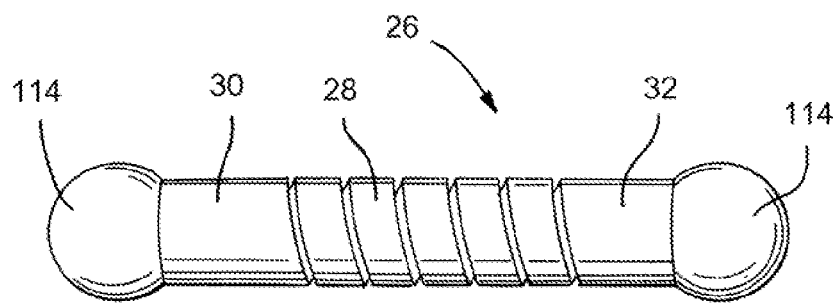
FIG. 15A shows a dynamic rod for use with the bone anchor of FIGS. 8-13, wherein the dynamic rod includes ball shaped members on its ends.

FIG. 15A shows a basic rod 26 that generally comprises a shaft with a flexible elastic central portion 28, a first end 30, and a second end 32. Ball-shaped members 114 are provided on the first end 30 and second end 32 of the rod 26. The ball-shaped members are substantially spherical in the disclosed embodiment and are configured to engage the bearing surface of the rod bearing 112 retained within the bone anchor 24. Exemplary bone anchors 24 configured to retain rod bearings for use with rods having ball-shaped ends are disclosed in FIGS. 8-13. In FIG. 15A, the ball shaped members 114 are formed integral with the rod in FIG. 15A. To this end, the ball-shaped members 114 may be molded as a single piece with the central dynamic portion 28 of the rod. Alternatively, the ball-shaped members 114 may be fixed to the dynamic portion 28 by other means, such as welding, adhesion, or other appropriate methods as will be recognized by those of skill in the art. In other alternative embodiments, the ball-shaped members 114 may be releasably connected to the dynamic portion 28. For example, the ball shaped members 114 may be screwed, snapped, or friction fit onto the rod 26 at the rod ends 30, 32. Those of skill in the art will recognize various other possibilities for securing the ball shaped members on the rod. In this embodiment, where the ball shaped members 114 are fixed relative to the dynamic portion 28, the rod 26 may be provided in numerous discrete lengths to accommodate size differences between different patients and/or different segmental units of the spine.

In an alternative embodiment, the ball shaped members 114 of the rod may be adjustably connected to the rod. With this arrangement, a single rod may be used to accommodate various size differences between patients and/or segmental units. Examples of rods 26 where the ball shaped member 114 is adjustable relative to the dynamic portion 28 are shown in FIGS. 15B-15F.

Figure 15B:
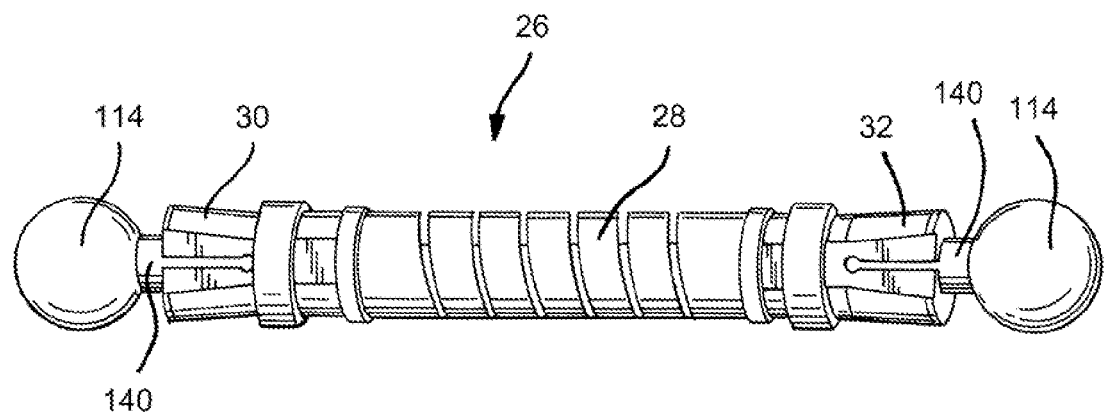
FIG. 15B shows an alternative embodiment of the dynamic rod of FIG. 15A wherein the length of the rod is adjustable.

In FIG. 15B, the ball-shaped members 114 are provided on posts 140. The posts 140 fit within the rod shaft, and particularly within a mouth 142 formed on the rod ends 30, 32. Each mouth 142 includes an upper jaw 144 and a lower jaw 146 that taper outwardly from the central axis of the rod. A passage is formed between the upper jaw 144 and the lower jaw that accepts one of the posts 140. A locking ring 148 is provided on each rod end 30, 32. When the locking ring 148 is moved over the mouth 142, the upper jaw 144 and lower jaw 146 of the mouth are forced together, thus compressing the post 140 within the mouth 142 and locking the associated ball member 114 on the end of the rod 26. Because the posts 140 and associated ball members 114 are slideable relative to the central dynamic portion 28 of the rod 26, the size of the rod may be adjusted to various lengths to accommodate different segmental units of the spine and patients of different sizes.

Figure 15C:
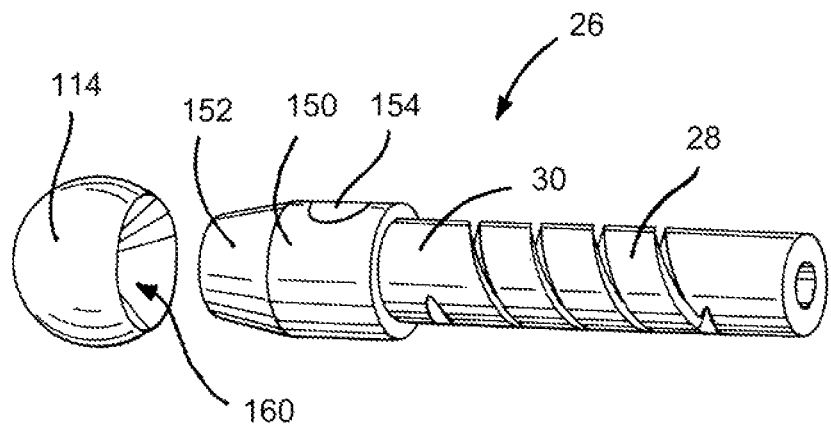
FIG. 15C shows another alternative embodiment of the dynamic rod of FIG. 15A wherein the length of the rod is adjustable.
Figure 15D:
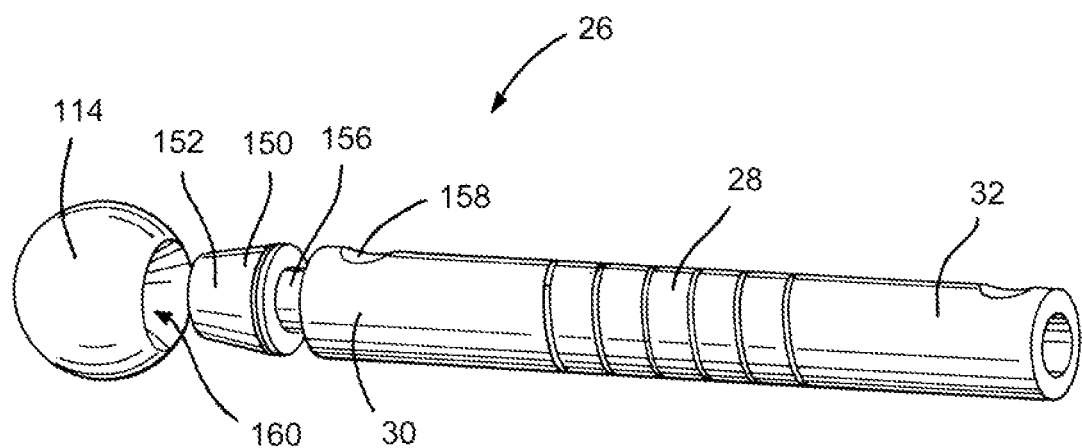
FIG. 15D shows yet another alternative embodiment of the dynamic rod of FIG. 15A wherein the length of the rod is adjustable.

In FIGS. 15C and 15D, the ball-shaped members 114 are taper-locked to a cap member 150 whose position can be adjusted to the desired length. In both of the embodiments of 15C and 15D, the cap member 150 includes a frusto-conical portion 152 that is inserted into a cavity 160 in the ball member 114 to taper-lock the ball member 114 to the cap member 150. Of course, in the embodiments of FIGS. 15C and 15D, another fastening means different from a taper-lock could be used to attach the ball member 114 to the cap member 150. In both embodiments of FIGS. 15C and 15D, the cap member 150 is secured to the rod using a setscrew. In the embodiment of FIG. 15C, the cap member fits over the cylinder of the rod, and a screw hole 154 is formed in the cap member 150. In the embodiment of FIG. 15D, a post 156 is inserted within the rod cylinder and a screw hole 158 is formed in the rod 26. Again, with both FIGS. 15C and 15D, because the ball members 114 are slideable relative to the central dynamic portion 28 of the rod 26, the size of the rod may be adjusted to various lengths to accommodate different segmental units of the spine and patients of different sizes.

Figure 15E:
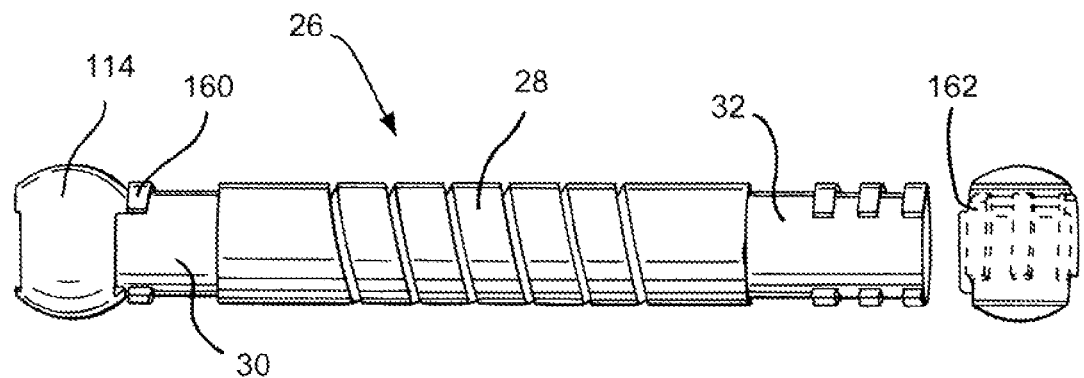
FIG. 15E shows another alternative embodiment of the dynamic rod of FIG. 15A wherein the length of the rod is adjustable.

In the embodiment of FIG. 15E spaced teeth 160 are provided on the rod ends 30, 32. Interlocking teeth 162 are also provided on the inside of the ball members 114. The teeth 160, 162 are provided with slight tapers such that the teeth 160 on the rod cylinder interact with the teeth 162 on the inside of the ball members 114. Depending on which set of spaced teeth 160, 162 are used, the length of the rod can be adjusted and fixed using a simple turn.

Figure 15F:
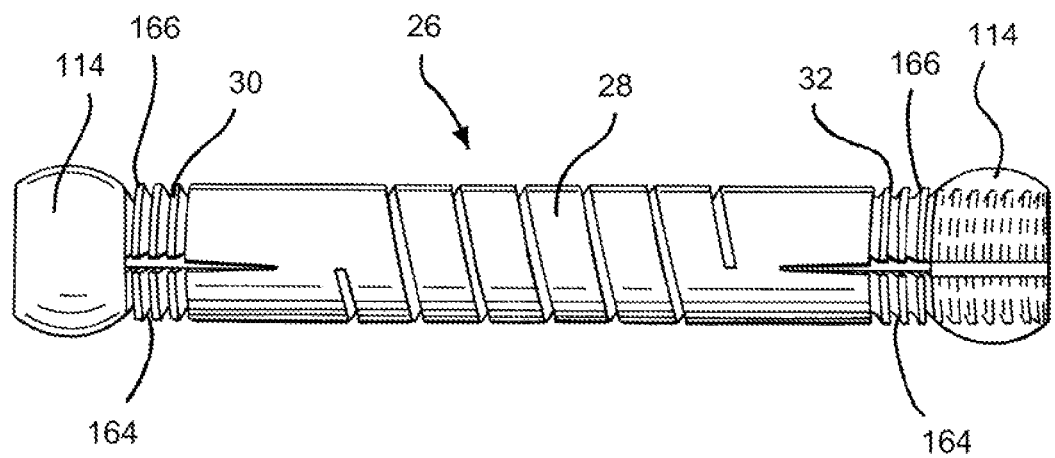
FIG. 15F shows yet another alternative embodiment of the dynamic rod of FIG. 15A wherein the length of the rod is adjustable.

In the embodiment of FIG. 15F, the rod ends are comprised of a shape memory alloy (also referred to as "smart metals" or "memory metals"), such as nickel-titanium (NiTi), copper-zinc-aluminum, or copper-aluminum-nickel. Shape memory alloys exhibit temperature dependent memory properties which may be advantageously used to lock the ball members 114 on the ends 30, 32 of the rod 26. In the embodiment of FIG. 15F, the ends 30, 32 of the rod include nested cups 166 comprised of a shape memory alloy. A slit 164 formed through the cups 166 along the end of the rod. Associated grooves are provided on the inside of the ball members. The ball members 114 are free to slide on the cups 166 on the rod ends 30, 32 at room temperature. However, at body temperature, the cups 166 splay outward, thus locking the cups 166 into the grooves on the inside of the ball member and securing the ball members in place.

Low Profile Design

Figure 16:
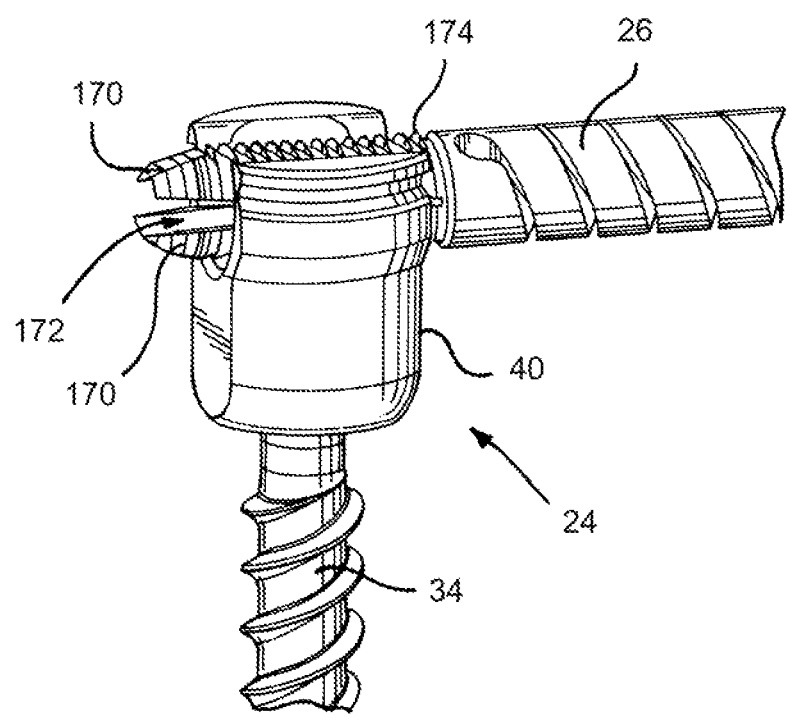
FIG. 16 shows a perspective view of an alternative embodiment of a bone anchor and rod for use with the spine stabilization system of FIG. 1 wherein the rod is secured to a cavity in the bone anchor without the use of a fixation screw.
Figure 17:
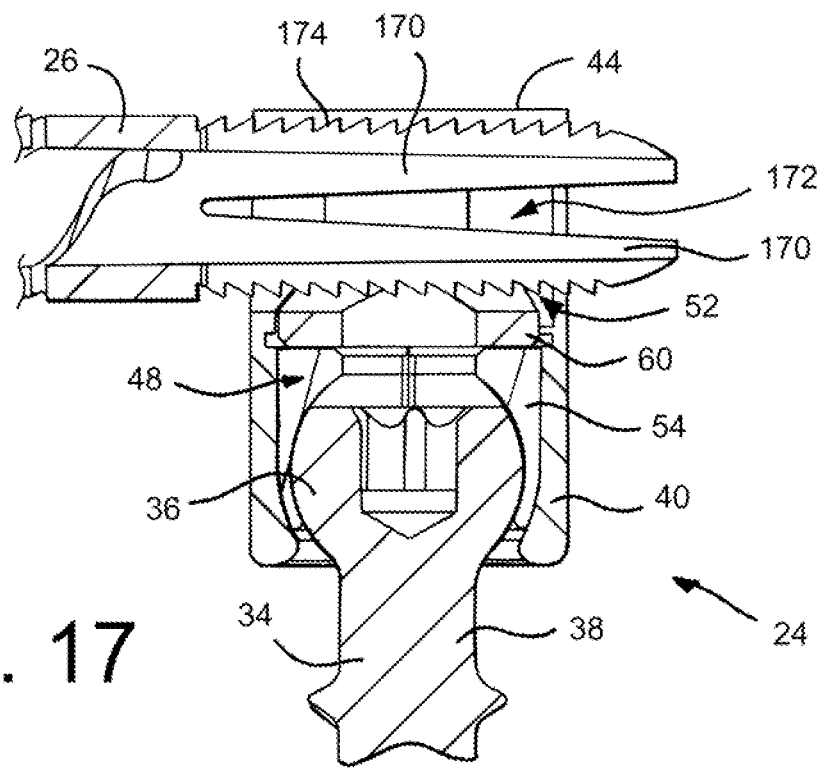
FIG. 17 shows a cross-sectional view of the bone anchor and rod of FIG. 16.
Figure 18:
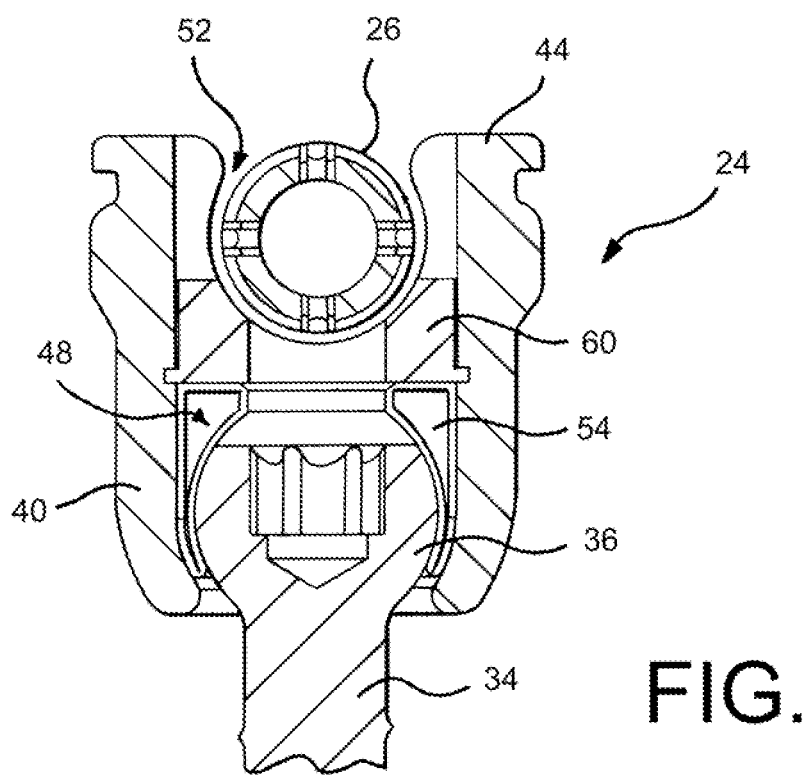
FIG. 18 shows a cross-sectional view of the bone anchor and rod of FIG. 17 rotated 90°.

FIGS. 16-18 show an alternative embodiment configured for use with any of the above-described designs where the pivot point of the rod is offset from the central or other axis defined by the rod (e.g., FIGS. 3-7). The advantage addressed in the embodiment of FIGS. 16-18 is that of a dynamic screw with a lower profile. In this embodiment, the lower portion of the bone anchor 24 is similar to that of FIGS. 3 and 4, and includes a bone screw cavity 48 configured to receive a bearing member 48 and the head 36 of a bone screw 34. An insert 60 is provided above the bearing member 54 that locks the bearing member in the cavity 48. Also similar to FIGS. 3 and 4, a rod cavity/passage 52 is provided above the insert. However, unlike FIGS. 3 and 4, no fixation screw is provided above the rod 26. Instead, the rod 26 and bone anchor 24 include features that allow the rod 26 to be locked into the rod cavity 52 without the use of a fixation screw.

In the exemplary embodiment of FIGS. 16-18 the locking features provided on the rod 26 include fingers 170 provided on the rod ends with slits 172 cut into each rod end between the fingers 170. Teeth 174 are also provided on the rod ends. The slits 172 allow the fingers 170 to contract toward each other as the end of the rod is forced into the rod cavity 52. Once the rod is in the cavity 52, the fingers 170 are flared back outwardly toward or past their original configuration. When the fingers are forced outwardly, they are pressed against the insert 60, including the teeth 174, thus locking the rod in place within the rod cavity. Flaring of the fingers may be achieved through the use of a memory metal or by other means, such as a wedge forced into the slits at the end of the rod. With the rod in place within the rod cavity 52, the rod presses against the insert 60 and receiver member 40, which locks the bearing 54 in place within the bone anchor 24. If the insert 60 is comprised of a relatively soft material, the teeth 174 may cut into the insert to assist in securing the rod within the bone anchor. In one alternative embodiment, the teeth 174 are designed to mate with complimentary teeth on insert 60 and receiver member 40 to assist in securing the rod within the bone anchor.

In one embodiment, a cap is provided over the superior end 44 of the bone anchor. This may be desirable if the rod will be passed through tissue. The cap could either be permanent or temporary. As best seen in FIG. 18, the distance across the rod cavity 52 generally decreases when moving from the center of the rod cavity toward the superior end 44. This decreased distance at the superior end 44 is less than the diameter of the rod 26, and helps in preventing passage of the rod through the top of the receiver member 40. However, if a cap were provided over the superior end 44 it could be used to further assist in retaining the rod 26 within the receiver member 40. Furthermore, if this embodiment were used in an minimally-invasive surgery procedure, where it would be more difficult to assure that the receiver members 40 are aligned in the correct configuration to properly engage and lock down the rod, the cap could mate with a feature on the screw head in such a way that it would insure that the heads are placed correctly and that the receiver member is properly secured.

Although the present invention has been described with respect to certain preferred embodiments, it will be appreciated by those of skill in the art that other implementations and adaptations are possible. For example, although the invention has been disclosed for use with reference to a single segmental spine unit, it could also be adapted for use with multi-level constructions. As another example, the dynamic rods disclosed herein include a helical flexible portion, but different dynamic rods may be used in other embodiments. As yet another example, the connection of the rod to the bone anchor may vary from those embodiments disclosed herein. Moreover, there are advantages to individual advancements described herein that may be obtained without incorporating other aspects described above. Therefore, the spirit and scope of the appended claims should not be limited to the description of the preferred embodiments contained herein.

What is claimed is:

1. A spine stabilization system comprising:
    at least one bone anchor assembly, the bone anchor assembly including a bone engaging member and a receiver member, wherein the receiver member includes at least one sidewall extending between an inferior end and a superior end, a connecting member cavity extending from a first sidewall portion of the at least one sidewall to a second sidewall portion of the at least one sidewall and a bone engaging member opening formed through the inferior end;
    an elongated connecting member defining a connecting member axis inserted into the connecting member cavity by moving the elongated connecting member along the connecting member axis through the first side of the receiver member without rotation of the connecting member and connected to the receiver member, wherein the connecting member comprises locking features monolithic with the connecting member, the locking features are configured to secure the connecting member to the receiver member without the use of a fixation screw extending through a top portion of the receiver member; and wherein at least one of the locking features includes at least one finger having a plurality of teeth, the at least one finger is configured to elastically flare away from the connecting member axis in order to secure the connecting member within the receiver member.

2. The spine stabilization system of claim 1 wherein the bone engaging member comprises a head and a shank, wherein the head is positioned within the receiver member and the shank extends from the inferior end of the receiver member.

3. The spine stabilization system of claim 2, further comprising:
    an insert adjacent to the connecting member cavity and configured to engage the plurality of teeth on the elongated connecting member.

4. The spine stabilization system of claim 3, wherein the insert is constructed of a material softer than the elongated connecting member such that the plurality of teeth on the elongated connecting member cut into the insert.

5. The spine stabilization system of claim 1, further comprising:
    a wedge inserted within a slot in the elongated connecting member and forcing the at least one finger to flare outwardly.

6. A spine stabilization system comprising:
    at least one bone anchor assembly, the bone anchor assembly including a bone engaging member and a receiver member, wherein the receiver member includes at least one sidewall extending between an inferior end and a superior end, a connecting member cavity extending from a first sidewall portion of the at least one sidewall to a second sidewall portion of the at least one sidewall and a bone engaging member opening formed through the inferior end;
    a monolithic elongated connecting member defining a connecting member axis inserted into the connecting member cavity, the elongated member including a slotted portion with a slot extending parallel to the connecting member axis and positioned within the connecting member cavity, the slotted portion forced away from the connecting member axis into engagement with the receiver member; and wherein the connecting member comprises: a plurality of teeth positioned within the connecting member cavity and engaged with the receiver member.

7. The spine stabilization system of claim 6 wherein:
the bone engaging member comprises a head and a shank;
the head is positioned within the receiver member; and
the shank extends from the inferior side of the receiver member.

8. The spine stabilization system of claim 7, further comprising:
  an insert adjacent to the connecting member cavity and configured to engage the plurality of teeth on the elongated connecting member.

9. The spine stabilization system of claim 8, wherein the insert is constructed of a material softer than the elongated connecting member such that the plurality of teeth on the elongated connecting member cut into the insert.

10. The spine stabilization system of claim 6, further comprising:
  a wedge inserted within a slot in the elongated connecting member to force the slotted portion away from the connecting member axis.

* * * * *